United States Patent [19]
Bokros

[11] 4,038,703
[45] Aug. 2, 1977

[54] PROSTHETIC DEVICES HAVING A REGION OF CONTROLLED POROSITY

[75] Inventor: Jack C. Bokros, San Diego, Calif.

[73] Assignee: General Atomic Company, San Diego, Calif.

[21] Appl. No.: 631,868

[22] Filed: Nov. 14, 1975

[51] Int. Cl.² .......................... A61F 1/22; A61F 1/24
[52] U.S. Cl. ........................................ 3/1.5; 3/1.4; 3/1.91; 3/1.911; 3/1.913; 128/92 C; 128/92 BC; 128/92 CA
[58] Field of Search ............ 3/1, 1.4, 1.5, 1.9–1.913; 128/92 C, 92 CA, 92 B, 92 BC; 32/10 A

[56] References Cited

U.S. PATENT DOCUMENTS

| 3,435,526 | 4/1969 | Brancato | 32/10 A |
| 3,546,711 | 12/1970 | Bokros | 3/1.5 |
| 3,839,741 | 10/1974 | Haller | 3/1.5 |
| 3,906,550 | 9/1975 | Rostoker et al. | 3/1.9 X |

FOREIGN PATENT DOCUMENTS 560,269 9/1957 Belgium .......................... 32/10 A Primary Examiner—Ronald L. Frinks
Attorney, Agent, or Firm—Fitch, Even, Tabin & Luedeka

[57] ABSTRACT

An improved prosthetic device having its exterior surface formed to provide a region of controlled porosity to promote the ingrowth of bone and/or tissue. A metal coil spring is secured to a metal substrate at a plurality of points, as by being disposed in a groove having a depth about equal to the loop diameter of the spring. Adjacent loops of the spring are preferably spaced apart from one another, and adjacent side-by-side spring sections may be interleaved with one another, with the interleaved loops being affixed to each other by common bonds at their points of junction.

14 Claims, 11 Drawing Figures

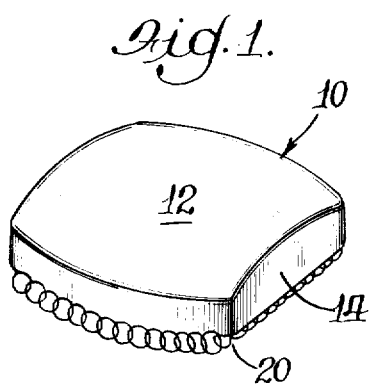
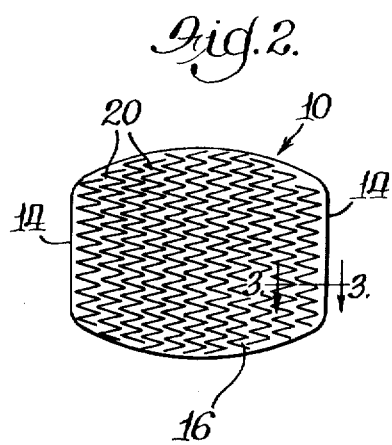
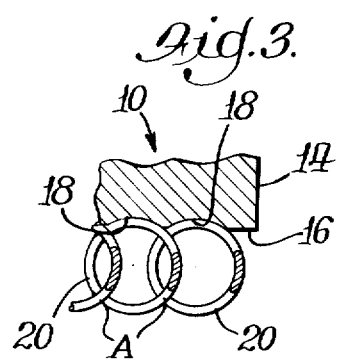
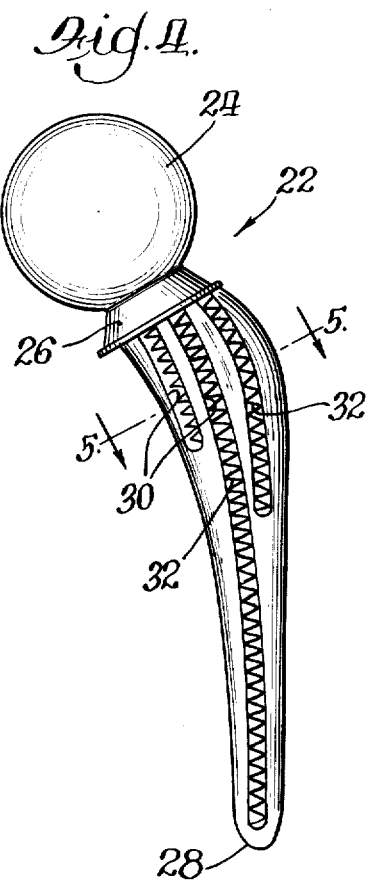
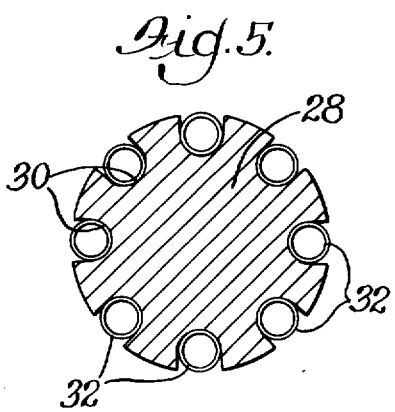
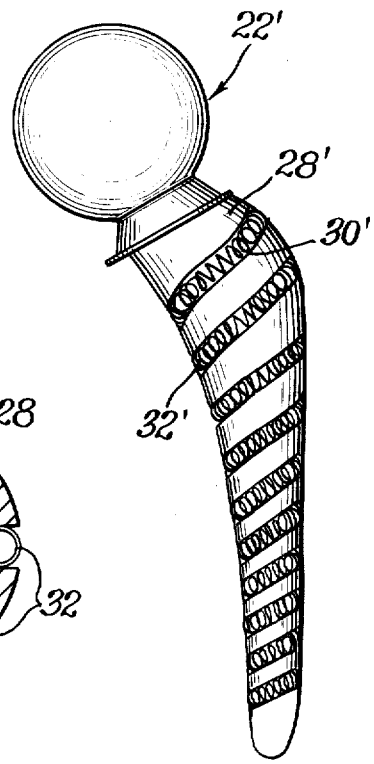
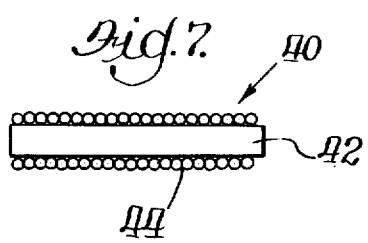

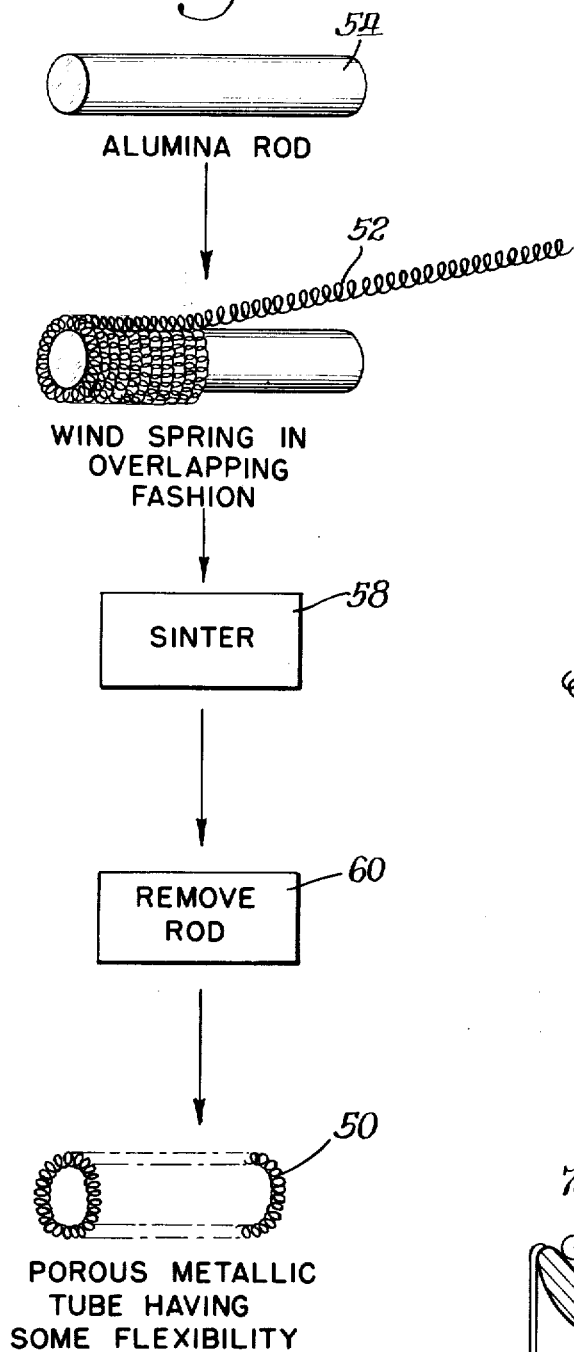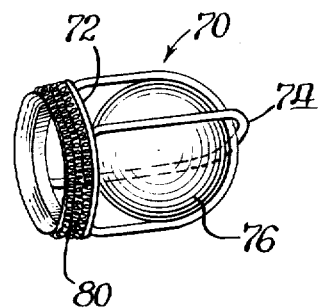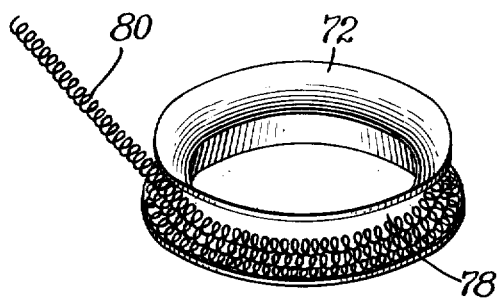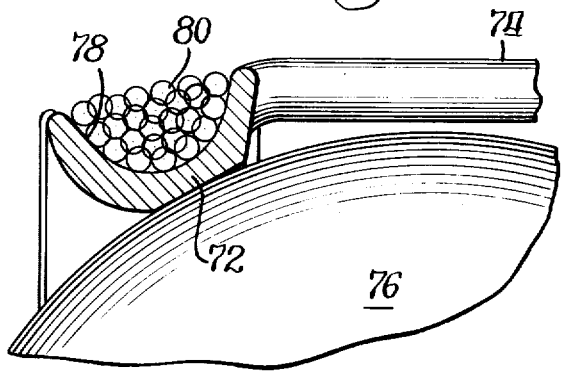

PROSTHETIC DEVICES HAVING A REGION OF CONTROLLED POROSITY

The present invention relates to prosthetic devices and, more particularly, primarily to prosthetic devices designed for use in the orthopedic area.

The use of prosthetic devices for repair or replacement of bone structure in living bodies is well known, as well as for replacements in the vascular system, for example artificial heart valves. Heretofore conventional prosthetic devices have been constructed from mtals, ceramics and plastics, depending upon their intended applications, and chemical-vapor-deposited carbon, particularly pyrolytic carbon, has now become more widely used for coating substrates to provide a dense exterior surface that is nonthrombogenic and biocompatible in the construction of prosthetic devices. More recently, other methods of vapor deposition for carbon, for example electron-beam heating in a vacuum have been used for coating applications. However, there remains the functional interrelationship between the device being implanted in the body and the remainder of the body, which is of a complex, biologically intricate nature, and the desire is such to provide prosthetic devices which will facilitate more uniform and stronger joinder to the adjacent body parts.

It is an object of the present invention to provide an improved prosthetic device well suited for use within the environment of the skeletal structure of a living body and which is capable of establishing a firm bond thereto.

Another object of the invention is to provide a prosthetic device having an exterior surface portion of carefully controlled and uniform porosity so as to promote the ingrowth of tissue and/or bone structure and thereby create long-lasting joinder.

A further object is to provide an improved method for making a prosthetic device having a surface of carefully controlled and uniform porosity which device may be of substantially any size and/or shape as needed to provide an effective body repair part.

These and other objects of the invention will be apparent when the following detailed description is read in conjunction with the accompanying drawings wherein:

FIG. 1 is a perspective view of a portion of a knee joint prosthesis;

FIG. 2 is a bottom view showing the knee joint prosthesis of FIG. 1;

FIG. 3 is an enlarged, fragmentary, sectional view taken along the line 3—3 of FIG. 2;

FIG. 4 is a front view showing a ball-containing portion of a hip joint prosthesis;

FIG. 5 is an enlarged sectional view taken along line 5—5 of FIG. 4;

FIG. 6 is a view similar to FIG. 4 showing an alternative embodiment of such a hip joint prosthesis;

FIG. 7 is a sectional view through a bone pin;

FIG. 8 is a diagrammatic representation showing the formation of a tubular prosthetic device structure having closely controlled porosity;

FIG. 9 is a perspective view showing a Starr-Edwards ball-type heart valve which has been modified in accordance with the present invention;

FIG. 10 is a diagrammatic view showing the application of a fine helical coil spring to the base of the valve shown in FIG. 9 by winding the same thereabout; and FIG. 11 is an enlarged fragmentary sectional view showing the heart valve of FIG. 9 with the ball located in closed position.

Basically, it has been found that the use of metallic wire coil springs provides an opportunity to create different surface configurations of uniform and carefully controlled porosity. It has been found that if prosthetic devices are provided with surfaces of controlled porosity at locations where attachment to tissue and/or bone is desired, ingrowth of tissue or bone into such porous surfaces occurs, resulting in excellent ultimate joinder of the prosthetic device to the adjacent parts of the living body. Whereas some previous attempts have been made to provide controlled porosity in prosthetic devices, the use of helical coil springs has been found not only to provide a ready and relatively inexpensive solution to the problem but to also provide a porous surface region the porosity of which can be precisely controlled.

Shown in FIG. 1 of the drawings is a knee joint prosthesis 10 designed for replacement of a seriously damaged knee. The prosthesis 10 has a pivotal wear surface 12 which is of generally arcuate shape and which is flanked by a pair of generally flat side surfaces 14. The arcuate surface 12 is designed for pivoting against another such arcuate wear surface in the functioning of the knee joint, and there is only a slight curvature between the lateral sides 14 in order to restrict pivoting in that direction and thus attempt to stabilize the knee joint against sideward movement.

The prosthesis 10 has an undersurface 16 which is nominally flat but which is provided with a plurality of parallel shallow grooves 18. In the illustrated embodiment, the grooves 18 run from the front to the rear of the prosthesis; however, it should be understood that the parallel grooves could also run from side-to-side, diagonally or in any desired direction. As best seen in FIG. 3, there is a helical coil spring 20 disposed in each of the grooves 18, and the grooves are so located that the adjacent helical coil springs 20 interleave or overlap with one another so that the individual loops or sections of each spring 20 extend into the helix of the next adjacent spring. The grooves 18 accordingly have a depth less than one-half the loop diameter of the springs 20. The prosthesis 10 may be formed by machining a suitable block of corrosion-resistant metal, and usually metal alloys such as stainless steel, Vitallium, and cobalt alloys, for example, Haynes alloy No. 25, or titanium are employed. The coil spring 20 is preferably made from the same metal as the remainder of the prosthesis; however, in some cases dissimilar metals are sometimes employed.

Generally a spring 20 is chosen which is formed so that the adjacent loops of the helix abut one another. As a result, when the springs 20 are stretched so that the loops spread apart and then are interleaved with the loops of an adjacent helical spring, the inherent compression characteristics causes adjacent springs to grasp one another at the points of contact when the elongating force is removed. In forming the prosthesis 10, a helical spring of suitable length would be disposed in each of the shallow grooves 18 and in such grasping contact with the adjacent springs. The block and spring assembly may then be held together, using a suitable jig, and heated to a sintering temperature under a non-oxidizing atmosphere, preferably hydrogen or vacuum. During sintering, the portions of the loops of the helix lying in each groove 18 are sintered to the curved surface of the block, while at the same time the touching loops of the helical springs 20 are sintered to one another at the points of touching, marked A in FIG. 3.

It should be understood that the use of such helical coil springs 20 allows the porosity of the surface to be controlled by the regulation of several parameters. Change in porosity can be accomplished by varying the wire diameter of the metal from which the coil springs are fabricated, by varying the loop diameter of the individual helices and by varying the amount of overlap or interleaving between adjacent springs. Moreover, porosity can be changed by stretching the individual springs to a greater degree so as to provide spacing of a greater distance between loops; however, such stretching to achieve porosity variance is more suitable to the constructions described hereinafter than to the creation of a surface such as that depicted in FIGS. 1 through 3 wherein the interleaving of adjacent springs occurs.

For replacement of a damaged knee joint, the natural bone joint portion corresponding to the prosthesis 10 is surgically removed, and the remaining end of the bone is shaped to provide a mating face that will fit with the undersurface of the prosthesis that is provided by the coil spring arrangement. The uniform and controlled porosity of the undersurface is conducive to the growth of natural bone and tissue in adherence thereto, and its presence induces acceptance of the replacement prosthesis as a functionally permanent section of the bone itself.

Depending upon the specific application, the prosthesis 10 can be used in its metallic form, or the entire exterior surface thereof can be coated with a more biocompatible material, such as vapor-deposited carbon or certain polymers. The use of chemical-vapor-deposited carbon as a coating for prosthetic devices generally is disclosed in U.S. Pat. No. 3,526,005, issued Sept. 1, 1970 in the names of Jack C. Bokros, et al. A preferred method for assuring good adhesion of a vapor-deposited coating to a metallic substrate is taught in pending U.S. patent application Ser. No. 527,971, filed Nov. 29, 1974 in the names of Jack C. Bokros, et al., now U.S. Pat. No. 3,952,334, issued Apr. 27, 1976, which application teaches the use of an intermediate layer of a high-temperature polymer, for example, a polyimide resin or a (polyamide-imide) resin, together with non-chemical vapor-deposition methods, such as vacuum evaporation or sputtering from a pure carbon source. Generally, the outer layer of vapor-deposited carbon need only be a fraction of a micron thick, and if such an intermediate polymer layer between about 0.2 and 10 microns thick is used, the thickness of the vapor-deposited carbon layer may be used thin as about 0.2 micron for carbon having a density of at least 1.6 g./cm$^3$.

Shown in FIG. 4 is a hip joint prosthesis 22 which has a ball section 24 fabricated from a suitable metal or ceramic material which is suitably proportioned and polished to provide a low friction surface for installation within the hip socket of a living person. Fastened to the ball section 24 is depending collar 26 and shank section 28, preferably formed of metal, which may be joined thereto in any suitable manner (not shown), as by providing the shank 28 and collar 26 with a short threaded stub at its upper end which mates with a threaded hole provided internally within the ball. The tapered shank 28 is designed for insertion into the upper end of the femur which is being partially replaced by the prosthesis.

The outer surface of the shank 28 is provided with a plurality of channels or grooves 30 which extend longitudinally thereof. Because of the tapered configuration of the shank 28, there are more channels 30 at the upper end than near the lower end thereof. An individual helical coil spring 32 of constant loop diameter is disposed in each of the channels 30 to provide the porous surface region into which bone fibers may grow. As illustrated in FIG. 5, the depth of the channels is preferably near the loop diameter of the spring; however, in specialized cases it may be appropriate to use a shallow groove or even none at all. The channels 30 should not have a depth greater than 150% of the diameter of the helical springs 32.

The individual springs 32 may be initially located in the channels in any suitable manner; however, inasmuch as they are mounted throughout 360° about the surface of the shank, initial spot welding of the ends is sometimes employed. Moreover, such spot welding facilitates slightly stretching helical springs, which are originally formed with their individual loops touching one another, so as to slightly lengthen the springs and thus provide a predetermined amount of spacing between the individual loops thereof, equal to at least about 10% of the diameter of the spring wire. After the initial assembly is completed so that each of the springs 32 lies in its respective channel 30, a suitable sintering operation is carried out so that the touching portion of each spring loop becomes permanently bonded to the metal surface of the channel in the shank section 28, thus securing the spring to the substrate at a plurality of spaced points.

FIG. 6 depicts an alternative embodiment of a hip joint prosthesis 22' to that depicted in FIGS. 4 and 5, and accordingly like reference numerals are employed for the same parts. In this embodiment, instead of having a plurality of longitudinally extending channels or grooves, a shank section 28' is provided which is provided with a single spiral channel 30' which runs continuously from a location near the top of the shank to the bottom thereof. A long coil spring 32' is used, and it may be suitably spot-welded at its one end to a location near the upper end of the channel 30' in the shank. Thereafter it is wrapped around and around the shank 28' along the spiral path, until it reaches the bottom end of the channel. Wrapping is carried out with the desired amount of tension in the spring 32' so as to spread apart the individual loops and to provide an amount of spacing to achieve the porosity which is desired. Thereafter, a sintering operation is carried out so as to bond the touching portions of the coil in the channel to the adjacent arcuate surface. Although the illustrated spacing between the adjacent convolutions of the spiral channel 30' machined in the metallic shank 28' is considered to be representative, this spacing can be increased or decreased, as desired, so as to vary the percentage of porous region provided on the shank portion of the prosthesis 22'. Conceivably the entire surface could be covered with a spiral winding of the spring 32', but likely a porous region this great in area would not be needed.

FIG. 7 depicts a simple bone pin 40 or the like wherein a cylindrical metallic rod 42 is inserted into the interior passageway through a helical spring 44 of constant diameter. The spring 44 should be proportioned so as not to be significantly oversize with regard to the outer diameter of the metal rod 42 so that a good bond will be created during the subsequent sintering operaion. Usually a coil spring 44 is chosen having an internal diameter which is substantially equal to the outer diameter of the rod, and after insertion, the spring is stretched the desired amount and tack-welded at each end prior to sintering. The individual loops of the spring are spaced apart at least about 10% of the diameter of the spring wire, and preferably the diameter of the spring wire is equal to between about 1 and about 5 percent of the diameter of the rod 42. Alternatively, a spring 44 may be chosen that has a slightly smaller internal diameter, in which case the spring is caused to unwrap slightly, by relative rotation of its opposite ends, to open up the diameter through the helical spring to a sufficient distance to accept the cylindrical rod 42. Thereafter, releasing the ends of the spring 44 causes it to firmly grasp the rod throughout its entire length and thereby obviates the need for tack-welding prior to sintering. In any event, once the sintering is completed, there are points of attachment between the spring and the surface of the rod throughout the lengths thereof.

FIG. 8 diagrammatically illustrates a process for forming a porous tube 50 which is generated by winding a long length of helical spring 52 of constant loop diameter about a suitable mandrel 54 and then joining the spring convolutions to one another to create a self-supporting structure. A suitable ceramic mandrel 54 is chosen, such as an alumina rod, which will not react with the metal spring at the sintering temperature and which has an external diameter equal to the internal diameter of the desired tube which is to be fabricated. The rod 54 may be somewhat greater in length than the tube 50 to be fabricated, and one end may be inserted in a lathe or the like so as to aid in its manipulation. One end of the spring 52 is suitably attached to the rod 54, and the helical spring is then wrapped spirally around the rod as the lathe slowly causes it to rotate, stretching the spring slightly to open up the loops and preferably to just slightly interleave the loops of one spiral convolution with the next. Wrapping is continued until the desired amount of length of the rod 54 is covered, and then the other end of the spring is also suitably affixed to the alumina rod.

Thereafter the assembly is transferred to a sintering station 58 where heating under an inert atmosphere is carried out so that the interleaved coils sinter to one another at the points of touching. There should be no significant reaction between the spring 56 and the ceramic mandrel 54 at the temperature employed. After sintering is complete, the bonds at the two ends are broken at an appropriate machining staion 60, and the alumina rod is removed from the interior of the coiled spring 56. The resultant product is a tubular structure 50 having a predetermined porosity, which is a function of the diameter of the spring wire, the loop diameter of the helix, the amount of stretching of the spring during its initial placement and the distance to which the spiral convolutions are interleaved with one another. The porous tubular structure 50 may be used as is, or it may be entirely coated, for example, with vapor-deposited carbon to make it more biocompatible.

As previously indicated, it may be desirable to provide an intermediate polymeric layer upon the coil spring wire and then coat that intermediate layer with vapor-deposited carbon. It will be recognized that such a one or two-step coating procedure will also slightly increase the diameter of the wire which constitutes the wound tubular structure 50, and such a coating operation can therefore be used to further decrease the porosity of the porous metallic tubular structure. Although there is a joinder of the loops of the adjacent convolutions of the wrapped structure, a limited amount of inherent resiliency remains so the tubular structure 50 is susceptible to some bending without fracturing.

Shown in FIG. 9 is a heart valve 70 of the Starr-Edwards design, the general details of which are described in U.S. Pat. No. 3,365,728, issued Jan. 30, 1968. The valve includes a base ring 72 upon which is mounted a cage 74 wherein there is disposed a ball valve member 76. The ring is preferably made of a non-corrodable metal, such as Stellite, and is shaped to provide an outwardly facing channel 78 about its outer periphery. Some type of a sleeve has previously been provided in the channel 78 to permit the heart valve 70 to be sutured in place in the body of the patient. However, in this embodiment of the invention, the sleeve is replaced by a wound helical spring.

As depicted in FIG. 10, an endless length of a very fine metal wire spring 80 has one end suitably attached to the channeled-surface of the ring, as by spot welding, and the helical spring is then wrapped around and around and around the outer periphery of the base ring so as to substantially fill the channel 78 with a plurality of convolutions of the spring. The spring 80 is slightly stretched so that the loops are spaced apart and interfit with one another as described with respect to FIG. 8. When wrapping is completed, the other end of the spring 80 is suitably welded to one of the earlier convolutions.

Thereafter, the base ring 72 with the fine spring wrapped around it is transferred to a sintering station where it is heated under an inert atmosphere so that the slightly interleaved coils sinter to one another at the points of touching. For a heart valve 70 to be implanted within a living human being, the helical spring 80 might be made from stainless steel wire between about 0.25 and 0.5mm in diameter which is coiled to have an outer loop diameter of about 2mm.

To improve biocompatibility, the base ring 72 with its wrapped and sintered spring 80 may be coated with vapor-deposited carbon. Thereafter, the ball valve member 76 and the cage 74 are mated with the base ring 72, and the struts of the cage permanently joined to the ring. In the implantation of the valve in the mitral position, the porous structure provided by the sintered spring assembly allows ready suturing to the tissue. Thereafter, the carboncoated porous spring structure provides a ready location for the ingrowth of tissue which unites the valve 70 to the heart and results in an excellent and secure affixing of the valve in place.

Although the invention has been illustrated and described with regard to certain preferred embodiments, it should be understood that changes and modifications as would be obvious to one having the ordinary skill in the art may be made without departing from the scope of the invention which is defined solely by the appended claims. Various of the features of the invention are set forth in the claims which follow.

What is claimed is:

1. An improved prosthetic device having an exterior surface formed at least in part to provide a region of controlled porosity to promote the ingrowth of bone and/or tissue, said device comprising a metal substrate plus metal coil spring means, said spring means being secured to said substrate at a plurality of spaced apart points and having adjacent loops which are spaced apart from one another, adjacent sections of said spring means being interleaved with one another with said interleaved loops being affixed to each other by common bonds at the points of junction thereof.

2. An improved prosthetic device in accordance with claim 1 wherein said substrate-coil spring means combination is coated with vapor-deposited carbon.

3. An improved prosthetic device of generally tubular configuration having a surface region of controlled porosity to promote the ingrowth of bone and/or tissue, said device comprising metal coil spring means spirally wound into a generally tubular shape with the loops of adjacent convolutions of said spring means being interleaved with one another and being secured to one another by common bonds at the points of junction therebetween.

4. An improved prosthetic device in accordance with claim 3 wherein said common bonds are sintered metal connections.

5. An improved prosthetic device in accordance with claim 4 wherein said spirally wound coil spring means is coated with vapor-deposited carbon.

6. A hip joint prosthesis comprising a ball section, a shank section which is formed of metal and has groove means formed therein, and metal coil spring means disposed in said groove means, which spring means is a helix of substantially constant diameter, said groove means has a depth not greater than about 150 percent of the diameter of said spring means, and said spring means being secured at a plurality of spaced-apart points to the surface of said shank section constituting said groove means.

7. An improved prosthetic device having an exterior surface formed at least in part to provide a region of controlled porosity to promote the ingrowth of bone and/or tissue, said device comprising a metal substrate plus metal coil spring means, said spring means being secured to said substrate at a plurality of spaced apart points, said substrate having a plurality of parallel grooves which have a depth less than one-half the loop diameter of said coil spring means, the loops of said spring means in each groove being interleaved with the loops of said spring means in the next adjacent groove, and said interleaved loops being affixed to each other by common bonds at the points of junction thereof.

8. An improved artificial heart valve, which device comprises a metal substrate in the form of an annular base ring having an outer surface portion which provides an annular channel plus metal coil spring means disposed in said channel and secured to the surface of said channel at a plurality of spaced apart points, said metal coil spring means being wrapped around in a plurality of convolutions and disposed so that the loops of adjacent convolution portions interleave with one another, with said interleaved loops being affixed to each other by common bonds at the points of junction thereof, the surface region formed by said spring means providing a region of controlled porosity to promote the ingrowth of tissue.

9. An improved heart valve in accordance with claim 8 wherein said common bonds are sintered metal connections and wherein said substrate-coil spring means combination is coated with vapor-deposited carbon.

10. An improved prosthetic device having an exterior surface formed at least in part to provide a region of conrolled porosity to promote the ingrowth of bone and/or tissue, which device comprises a metal substrate which is formed with groove means in a surface portion thereof plus metal coil spring means, said groove means having a depth not greater than 150 percent of the loop diameter of said spring means, and said spring means being disposed in said groove and being joined to the surface of said groove at a plurality of points along the length of said spring means.

11. An improved prosthetic device in accordance with claim 10 wherein said groove means has a depth which is near the loop diameter of said spring means.

12. An improved prosthetic device in accordance with claim 10 wherein said points of joinder are sintered connections and wherein said substrate-coil spring means combination is coated with vapor-deposited carbon.

13. An improved prosthetic device having an exterior surface formed at least in part to provide a region of controlled porosity to promote the ingrowth of bone and/or tissue, which device comprises a metal substrate having a substantially smooth cylindrical outer surface portion and metal coil spring means in the form of a helix of a constant diameter disposed generally coaxial therewith, the internal diameter of said helix being substantially equal to or slightly less than the exterior diameter of said cylindrical substrate portion so that said helix is in contact with said cylindrical portion along the length of said helix and affixed to said cylindrical surface by sintered connections, said spring wire being circular in cross section and having a diameter equal to between about 1 and about 5 percent of the diameter of said cylindrical portion, the individual loops of said helix in said coaxial disposition being spaced apart a distance equal to at least about 10 percent of the diameter of said spring wire.

14. An improved prosthetic device in accordance with claim 13 wherein said helix internal diameter is less than said cylindrical portion and wherein said sintered substrate-helix combination is coated with vapor-deposited carbon.

* * * * *